(12) United States Patent
Sato et al.

(10) Patent No.: US 12,139,457 B2
(45) Date of Patent: Nov. 12, 2024

(54) MODIFYING AGENT FOR POLYOLEFIN RESIN FILMS, COMPOSITION FOR POLYOLEFIN RESIN FILMS, MODIFIED POLYOLEFIN RESIN FILM, AND MULTILAYER FILM

(71) Applicant: TAKEMOTO YUSHI KABUSHIKI KAISHA, Aichi-ken (JP)

(72) Inventors: Shumma Sato, Gamagori (JP); Satoshi Oya, Gamagori (JP); Yusuke Nishi, Gamagori (JP)

(73) Assignee: TAKEMOTO YUSHI KABUSHIKI KAISHA, Gamagori (JP)

( * ) Notice: Subject to any disclaimer, the term of this patent is extended or adjusted under 35 U.S.C. 154(b) by 887 days.

(21) Appl. No.: 17/258,326

(22) PCT Filed: Jul. 8, 2019

(86) PCT No.: PCT/JP2019/027029
§ 371 (c)(1),
(2) Date: Jan. 6, 2021

(87) PCT Pub. No.: WO2020/013140
PCT Pub. Date: Jan. 16, 2020

(65) Prior Publication Data
US 2021/0269387 A1 Sep. 2, 2021

(30) Foreign Application Priority Data
Jul. 10, 2018 (JP) .................................. 2018-130697

(51) Int. Cl.
| | | |
|---|---|---|
| C07C 69/33 | (2006.01) | |
| C07C 69/58 | (2006.01) | |
| C07D 307/12 | (2006.01) | |
| C08K 5/103 | (2006.01) | |

(52) U.S. Cl.
CPC .............. *C07C 69/33* (2013.01); *C07C 69/58* (2013.01); *C07D 307/12* (2013.01); *C08K 5/103* (2013.01)

(58) Field of Classification Search
CPC ...................................................... C07C 69/33
See application file for complete search history.

(56) References Cited

U.S. PATENT DOCUMENTS

2014/0162922 A1  6/2014  Verhaeghe et al.

FOREIGN PATENT DOCUMENTS

| | | |
|---|---|---|
| JP | S5879044 A | 5/1983 |
| JP | S59161447 A | 9/1984 |
| JP | S60229951 A | 11/1985 |
| JP | S61157558 A | 7/1986 |
| JP | S62220552 A | 9/1987 |
| JP | H0596694 A | 4/1993 |
| JP | H05222252 A | 8/1993 |
| JP | H08199156 A | 8/1996 |
| JP | 2000007854 | 1/2000 |
| JP | 2000007854 A | 1/2000 |
| JP | 2001213975 A | 8/2001 |
| JP | 2001320980 A | 11/2001 |
| JP | 2004115600 A | 4/2004 |
| JP | 2005036088 A | 2/2005 |
| JP | 2006231899 A | 9/2006 |
| JP | 2008156530 A | 7/2008 |
| JP | 2008248216 A | 10/2008 |
| JP | 2008266463 A | 11/2008 |
| JP | 2009101606 A | 5/2009 |
| JP | 2009185123 A | 8/2009 |
| JP | 2010132926 A | 6/2010 |
| JP | 2015004032 A | 1/2015 |
| JP | 2016060909 A | 4/2016 |
| JP | 2017075199 | 4/2017 |
| JP | 2017075199 A | 4/2017 |
| JP | 2017179350 | 10/2017 |
| JP | 2017179350 A | 10/2017 |
| WO | 2020013140 A1 | 1/2020 |

OTHER PUBLICATIONS

English machine translation of Goto et al. (JP 2000-7854). (Year: 2000).*
International Search Report issued in International Application No. PCT/JP2019/027029 mailed Sep. 17, 2019; 2 pages.
Extended European Search Report for Application No. 19834017.6 mailed Mar. 3, 2022.

* cited by examiner

*Primary Examiner* — Michael F Pepitone
(74) *Attorney, Agent, or Firm* — CANTOR COLBURN LLP

(57) ABSTRACT

Modifying agents for polyolefin resin films include a partial ester of a tri- to hexahydric polyol with a straight chain aliphatic carboxylic acid having 8 to 22 carbon atoms. The partial ester contains 70% by mass or more in total of monoesters and diesters. The mass ratio of the monoester content to the diester content is monoester/diester mass=30/70 to 86/14. This modifying agent for polyolefin resin films is applied to a polyolefin resin film in which the content of a diethanolamine compound having an alkyl group or alkenyl group having 8 to 22 carbon atoms or a diethanolamide compound having an alkyl group or alkenyl group having 8 to 22 carbon atoms is 0.02% by mass or less, and the content of an alkylsulfonic acid alkali metal salt is 0.004% by mass or less.

11 Claims, No Drawings

MODIFYING AGENT FOR POLYOLEFIN RESIN FILMS, COMPOSITION FOR POLYOLEFIN RESIN FILMS, MODIFIED POLYOLEFIN RESIN FILM, AND MULTILAYER FILM

CROSS REFERENCE TO RELATED APPLICATIONS

This application is a National Phase application of International Application No. PCT/JP2019/027029 filed on Jul. 8, 2019, which claims priority to Japanese Patent Application No. 2018-130697 filed on Jul. 10, 2018, which are incorporated by reference in their entireties.

TECHNICAL FIELD

The present invention relates to a modifying agent for a polyolefin resin film capable of imparting excellent antifogging property to a polyolefin resin without adversely affecting transparency and film forming stability of a polyolefin resin film, a composition for a polyolefin resin film containing the modifying agent, a modified polyolefin resin film formed by using the composition for a resin film, and a laminated film having the modified polyolefin resin film as at least one surface layer thereof.

BACKGROUND ART

Films formed of polyolefin resin compositions are broadly used, for example, as packaging materials. For polyolefin resins, which intrinsically has hydrophobic properties, polyolefin resin modifying agents that contain a surfactant or the like are sometimes used from the viewpoint of preventing charging and fogging due to static electricity.

Conventionally, polyolefin resin modifying agents disclosed, for example, in Patent Documents 1 to 3 are known. Patent Document 1 discloses a constitution containing a polyglycerol fatty acid ester. Patent Document 2 discloses a constitution containing a monoester of glycerol with a fatty acid having 8 to 22 carbon atoms, a monoester of diglycerol with a fatty acid having 8 to 22 carbon atoms, a polyoxyethylene alkylamino ether, and a monoester or a mixture of a monoester and a diester of a polyoxyethylene alkylamino ether with a fatty acid having 8 to 22 carbon atoms. Patent Document 3 discloses a constitution containing an ester of glycerol with a fatty acid, an ester of polyglycerol with a fatty acid, and an ester of diglycerol with a fatty acid.

PRIOR ART LITERATURE

Patent Literature

Patent Document 1: Japanese Laid-Open Patent Publication No. 05-096694
Patent Document 2: Japanese Laid-Open Patent Publication No. 2006-231899
Patent Document 3: Japanese Laid-Open Patent Publication No. 2017-179350

SUMMARY OF THE INVENTION

Problem to be Solved by the Invention

However, there is a problem that, although these conventional modifying agents are capable of imparting adequate antifogging property to polyolefin resin films, the transparency and the film forming stability of the polyolefin resin films may be decreased.

The problem to be solved by the present invention is to provide a modifying agent for a polyolefin resin film capable of imparting excellent antifogging property to a polyolefin resin film without adversely affecting transparency and film forming stability, a composition for a polyolefin resin film containing the modifying agent, a modified polyolefin resin film formed by using the composition for resin film, and a laminated film having the modified polyolefin resin film as at least one surface layer thereof.

Means for Solving the Problem

As a result of studies to solve the above problem, the inventors of the present invention have found that a modifying agent for a polyolefin resin film that contains a specific nonionic surfactant is surely suitable.

In order to solve the above problem, a modifying agent for a polyolefin resin film of a first aspect of the present invention is a partial ester of a tri- to hexahydric polyol with a straight chain aliphatic carboxylic acid having 8 to 22 carbon atoms, wherein the partial ester contains 70% by mass or more in total of monoester and diester, and the mass ratio of the content of the monoester to the content of the diester is monoester/diester=30/70 to 86/14, wherein the modifying agent for a polyolefin resin film is applied to a polyolefin resin film in which the content of a diethanolamine compound having an alkyl group or alkenyl group having 8 to 22 carbon atoms or a diethanolamide compound having an alkyl group or alkenyl group having 8 to 22 carbon atoms is 0.02% by mass or lower, and the content of an alkylsulfonic acid alkali metal salt is 0.004% by mass or lower.

In the modifying agent for a polyolefin resin film, the mass ratio of the content of the monoester to the content of the diester is preferably monoester/diester=40/60 to 86/14.

In the modifying agent for a polyolefin resin film, the permeation amount of the partial ester is preferably 20 mg/g or larger.

In the modifying agent for a polyolefin resin film, the HLB of the partial ester is preferably 2 to 8.5.

In the modifying agent for a polyolefin resin film, the polyol is preferably diglycerol.

It is preferable that the modifying agent for a polyolefin resin film is applied to a polyolefin resin film substantially free of the diethanolamine compound or the diethanolamide compound and the alkylsulfonic acid alkali metal salt.

With regard to the modifying agent for a polyolefin resin film, the polyolefin resin film is preferably a film for food.

A composition for a polyolefin resin film of another aspect of the present invention contains 0.1% to 30% by mass of the modifying agent for a polyolefin resin film.

A modified polyolefin resin film of another aspect of the present invention contains 0.1% to 5% by mass of the modifying agent for a polyolefin resin film, wherein in the film, the content of a diethanolamine compound having an alkyl group or alkenyl group having 8 to 22 carbon atoms or a diethanolamide compound having an alkyl group or alkenyl group having 8 to 22 carbon atoms is 0.02% by mass or lower, and the content of an alkylsulfonic acid alkali metal salt is 0.004% by mass or lower.

In the modified polyolefin resin film, the haze value is preferably lower than 10%.

A laminated film of another aspect of the present invention has a film layer that contains the modifying agent for a polyolefin resin film as at least either one surface layer thereof, wherein the laminated film contains 0.01% to 5% by mass of the modifying agent for a polyolefin resin film.

Effect of the Invention

The present invention succeeds in imparting the antifogging property without adversely affecting transparency and film forming stability.

MODES FOR CARRYING OUT THE INVENTION

First Embodiment

A first embodiment that embodies a modifying agent for a polyolefin resin film according to the present invention (hereinafter referred to simply as modifying agent) will now be described. A modifying agent of the present embodiment contains a partial ester of a tri- to hexahydric polyol with a straight chain aliphatic carboxylic acid having 8 to 22 carbon atoms.

In the partial ester of a tri- to hexahydric polyol with a straight chain aliphatic carboxylic acid having 8 to 22 carbon atoms, specific examples of the tri- to hexahydric polyol used as a raw material include (1) polyhydric alcohols, such as glycerol, pentaerythritol, sorbitol, and glucose, (2) cyclic ether polyhydric alcohols obtained by dehydration of sorbitol, such as sorbitan and sorbide, (3) (poly)ether tetraols, such as diglycerol and ethylene glycol diglyceryl ether, (4) (poly)ether pentaols, such as triglycerol and trimethylolpropane diglyceryl ether, and (5) (poly)ether hexaols, such as tetraglycerol and dipentaerythritol.

Specific examples of the straight chain aliphatic carboxylic acid having 8 to 22 carbon atoms used as a raw material include caprylic acid, pelargonic acid, capric acid, undecylic acid, undecylenic acid, lauric acid, tridecyl acid, myristic acid, pentadecylic acid, palmitic acid, margaric acid, stearic acid, arachidic acid, henicosylic acid, docosanoic acid, oleic acid, linolic acid, linolenic acid, erucic acid, 12-hydroxystearic acid, and ricinoleic acid.

The partial ester of a tri- to hexahydric polyol with a straight chain aliphatic carboxylic acid having 8 to 22 carbon atoms contains 70% by mass or more in total of monoester and diester. The mass ratio of the content of the monoester to the content of the diester is monoester/diester=30/70 to 86/14 and preferably monoester/diester=40/60 to 86/14. By specifying the monoester/diester in the numerical value range, the advantageous effects of the present invention, particularly the film forming stability can be further improved.

With respect to the combination of a tri- to hexahydric polyol with a straight chain aliphatic carboxylic acid having 8 to 22 carbon atoms, it is preferable that the polyol is diglycerol and the straight chain aliphatic carboxylic acid is at least one selected from straight chain aliphatic carboxylic acids having 8 to 22 carbon atoms. With this constitution, the advantageous effects of the present invention, particularly the antifogging property and the antistaticity can be further improved.

Specific examples of the partial ester of a tri- to hexahydric polyol with a straight chain aliphatic carboxylic acid having 8 to 22 carbon atoms include partial esters of glycerol with caprylic acid, partial esters of glycerol with pelargonic acid, partial esters of glycerol with capric acid, partial esters of glycerol with undecylic acid, partial esters of glycerol with undecylenic acid, partial esters of glycerol with lauric acid, partial esters of glycerol with tridecylic acid, partial esters of glycerol with myristic acid, partial esters of glycerol with pentadecylic acid, partial esters of glycerol with palmitic acid, partial esters of glycerol with margaric acid, partial esters of glycerol with stearic acid, partial esters of glycerol with arachidic acid, partial esters of glycerol with henicosylic acid, partial esters of glycerol with docosanoic acid, partial esters of glycerol with oleic acid, partial esters of glycerol with ricinolic acid, partial esters of glycerol with linolenic acid, partial esters of glycerol with erucic acid, partial esters of glycerol with 12-hydroxystearic acid, partial esters of glycerol with ricinoleic acid, partial esters of diglycerol with caprylic acid, partial esters of diglycerol with pelargonic acid, partial esters of diglycerol with capric acid, partial esters of diglycerol with undecylic acid, partial esters of diglycerol with undecylenic acid, partial esters of diglycerol with lauric acid, partial esters of diglycerol with tridecylic acid, partial esters of diglycerol with myristic acid, partial esters of diglycerol with pentadecylic acid, partial esters of diglycerol with palmitic acid, partial esters of diglycerol with margaric acid, partial esters of diglycerol with stearic acid, partial esters of diglycerol with arachidic acid, partial esters of diglycerol with henicosylic acid, partial esters of diglycerol with docosanoic acid, partial esters of diglycerol with oleic acid, partial esters of diglycerol with ricinolic acid, partial esters of diglycerol with linolenic acid, partial esters of diglycerol with erucic acid, partial esters of diglycerol with 12-hydroxystearic acid, partial esters of diglycerol with ricinoleic acid, partial esters of sorbitan with caprylic acid, partial esters of sorbitan with pelargonic acid, partial esters of sorbitan with capric acid, partial esters of sorbitan with undecylic acid, partial esters of sorbitan with undecylenic acid, partial esters of sorbitan with lauric acid, partial esters of sorbitan with tridecylic acid, partial esters of sorbitan with myristic acid, partial esters of sorbitan with pentadecylic acid, partial esters of sorbitan with palmitic acid, partial esters of sorbitan with margaric acid, partial esters of sorbitan with stearic acid, partial esters of sorbitan with arachidic acid, partial esters of sorbitan with henicosylic acid, partial esters of sorbitan with docosanoic acid, partial esters of sorbitan with oleic acid, partial esters of sorbitan with ricinolic acid, partial esters of sorbitan with linolenic acid, partial esters of sorbitan with erucic acid, partial esters of sorbitan with 12-hydroxystearic acid, partial esters of sorbitan with ricinoleic acid, partial esters of tetraglycerol with caprylic acid, partial esters of tetraglycerol with pelargonic acid, partial esters of tetraglycerol with capric acid, partial esters of tetraglycerol with undecylic acid, partial esters of tetraglycerol with undecylenic acid, partial esters of tetraglycerol with lauric acid, partial esters of tetraglycerol with tridecylic acid, partial esters of tetraglycerol with myristic acid, partial esters of tetraglycerol with pentadecylic acid, partial esters of tetraglycerol with palmitic acid, partial esters of tetraglycerol with margaric acid, partial esters of tetraglycerol with stearic acid, partial esters of tetraglycerol with arachidic acid, partial esters of tetraglycerol with henicosylic acid, partial esters of tetraglycerol with docosanoic acid, partial esters of tetraglycerol with oleic acid, partial esters of tetraglycerol with ricinolic acid, partial esters of tetraglycerol with linolenic acid, partial esters of tetraglycerol with erucic acid, partial esters of tetraglycerol with 12-hydroxystearic acid, and partial esters of tetraglycerol with ricinoleic acid. These specific examples may be used singly or concurrently in two or more.

The partial ester of a tri- to hexahydric polyol with a straight chain aliphatic carboxylic acid having 8 to 22 carbon atoms can be produced by a well-known method. The production method is not especially limited, but examples thereof include a method of carrying out heating and transesterification in any inert gas atmosphere, such as nitrogen or carbon dioxide, without a catalyst added to a mixture of, for example, an oil or fat, and a tri- to hexahydric polyol, or with an alkali added thereto as a catalyst. The heating condition involves the processing in the temperature range of preferably about 180° C. to 260° C. and more preferably about 200° C. to 250° C. for preferably about 0.5 to 5 hours and more preferably about 1 to 3 hours. Examples of the alkali catalyst to be used here include potassium hydroxide, sodium hydroxide, potassium carbonate, and sodium carbonate. Examples of the production method alternatively include a method of carrying out heating and esterification reaction in any inert gas atmosphere, such as nitrogen or carbon dioxide, without a catalyst added to a mixture of a straight chain aliphatic carboxylic acid having 8 to 22 carbon atoms and a tri- to hexahydric polyol, or with an acid or an alkali added thereto as a catalyst, and neutralizing the catalyst after the finish of the reaction. The heating condition involves the processing in the temperature range of preferably about 180° C. to 260° C. and more preferably about 200° C. to 250° C. for preferably about 0.5 to 5 hours and more preferably about 1 to 3 hours. After the esterification reaction, there may be carried out treatments including removal of the unreacted tri- to hexahydric polyol, decolorization, and deodorization.

As methods of removing the unreacted tri- to hexahydric polyol from the reaction product and recovering a specific ester compound, well-known methods can be applied and include vacuum distillation, molecular distillation, column chromatography, and liquid-liquid extraction. The regulation of the monoester/diester ratio of the tri- to hexahydric polyol and the straight chain aliphatic carboxylic acid having 8 to 22 carbon atoms may be carried out by regulating the reaction condition and using obtained compounds as they are, or by weighing and mixing the specific ester compounds recovered by the above method. The contents of monoester and diester contained in the ester compounds can be measured by gel permeation chromatography.

The partial ester usable for a modifying agent of the present embodiment preferably has a permeation amount of 20 mg/g or larger. The permeation amount is an amount of the modifying agent immersed into a polyolefin resin, and can be calculated according to JIS K7114 "Plastics-Methods of test for the determination of the effects of immersion in liquid chemicals". Examples of the polyolefin resin to be used in measurement of the permeation amount includes an ethylene-(1-butene) copolymer (density: 0.920 g/cm$^3$, MFR: 2.1 g/10 min, ethylene copolymerization ratio: 95%). The JIS K7114 corresponds to ISO 175, published in 1999 as second version, Plastics-Methods of test for the determination of the effects of immersion in liquid chemicals, and technical contents of the both are equal.

The permeation amount of the partial ester of a tri- to hexahydric polyol with a straight chain aliphatic carboxylic acid having 8 to 22 carbon atoms is preferably 20 mg/g or larger. With the permeation amount of 20 mg/g or larger, the solubility of the modifying agent to the polyolefin resin can be raised and the film forming stability of the polyolefin resin film can be further improved.

The hydrophile-lipophile balance (HLB) of the partial ester usable for the modifying agent of the present embodiment is preferably 2 to 8.5 and more preferably 5 to 8.5. With HLB in the above range, a polyolefin resin film having better film forming stability and antifogging property can be obtained. In particular, with HLB of 2 or higher, the hydrophilicity of the modifying agent is high and therefore the antifogging property can be further improved. Further in particular, with HLB of 8.5 or lower, the compatibility with the polyolefin resin, which is hydrophobic, is raised and the film forming stability of the polyolefin resin film can be further improved.

The HLB value is a value to indicate the degree of affinity of a surfactant for water and oil, and in the present invention, there is adopted the numerical value by the Atras method, which is calculated by the following expression.

$$HLB = 20 \times (1 - S/A)$$ [Calculation Expression]

S: saponification value of ester
A: neutralization value of the ester

Specific examples of the polyolefin resin to which the modifying agent of the present embodiment is to be applied include (1) α-olefin homopolymers, such as polyethylene and polypropylene, obtained by using one selected from α-olefins having 2 to 8 carbon atoms, such as ethylene, propylene, 1-butene, 1-hexene, 4-methylpentene-1, and 1-octene, (2) α-olefin copolymers, such as ethylene/propylene copolymers, ethylene/1-butene copolymers, and ethylene/1-hexene copolymers, obtained by using two or more selected from α-olefins having 2 to 8 carbon atoms as described above, (3) copolymers obtained from ethylene and vinyl acetate, (4) ethylene/vinyl alcohol copolymers obtained by saponification of copolymers obtained from ethylene and vinyl acetate, (5) ethylene/acrylic acid copolymers obtained by using ethylene and one or more selected from acrylic acid, methyl acrylate, and ethyl acrylate, and (6) ethylene/methacrylic acid copolymers obtained by using ethylene and one or more selected from methacrylic acid and methyl methacrylate. Among these, preferable are α-olefin copolymers of the above (2) which are copolymers of ethylene with α-olefins having 4 to 8 carbon atoms. More preferable are α-olefin copolymers of the above (2) which are copolymers containing 1% to 50% by mass of units constituted of the α-olefins having 4 to 8 carbon atoms. Any of such α-olefin copolymers are more preferably ones obtained by a gas phase method, a solution polymerization method or the like using a well-known homogeneous catalyst, such as a highly active Ziegler catalyst or a metallocene catalyst, and especially preferably ones having a density of 0.86 to 0.95 g/cm$^3$ and an MFR of 0.01 to 30 g/10 min. The olefin resins exemplified above may be used singly or as a mixture of two or more thereof.

The modifying agent of the present embodiment is applied to a polyolefin resin film in which the content of a diethanolamine compound having an alkyl group or alkenyl group having 8 to 22 carbon atoms or a diethanolamide compound having an alkyl group or alkenyl group having 8 to 22 carbon atoms is 0.02% by mass or lower, preferably 0.01% by mass or lower. More preferably, the modifying agent is applied to a polyolefin resin film substantially free of the diethanolamine compound or the diethanolamide compound. "Substantially free of the diethanolamine compound or the diethanolamide compound" means that the diethanolamine compound or the diethanolamide compound are not incorporated specially, and does not exclude the diethanolamine compound or the diethanolamide compound contained as an impurity in a small amount in each raw material. With 0.01% by mass or lower of the diethanolamine compound or the diethanolamide compound in the polyolefin resin film, the transparency of the film can be improved.

The modifying agent of the present embodiment is applied to a polyolefin resin film in which the content of an alkylsulfonic acid alkali metal salt is 0.004% by mass or lower, preferably 0.001% by mass or lower. More preferably, the modifying agent is applied to a polyolefin resin film substantially free of the alkylsulfonic acid alkali metal salt. "Substantially free of the alkylsulfonic acid alkali metal salt" means that the alkylsulfonic acid alkali metal salt are not incorporated specially, and does not exclude the alkylsulfonic acid alkali metal salt contained as an impurity in a small amount in each raw material. With 0.004% by mass or lower of the alkylsulfonic acid alkali metal salt in the polyolefin resin film, the film forming stability of the film can be improved.

In the case where the modifying agent is applied to a multilayer film, the content of the diethanolamine compound or the diethanolamide compound and the content of the alkylsulfonic acid alkali metal salt in the film indicate contents in a layer in which the modifying agent is blended.

Applications of the polyolefin resin film to which the modifying agent of the present embodiment is applied are not especially limited. The polyolefin resin film to which the modifying agent of the present embodiment is applied is excellent in transparency and antifogging property, and therefore is applied preferably as a film for food.

Second Embodiment

A second embodiment that embodies a composition for a polyolefin resin film according to the present invention (hereinafter referred to simply as resin composition) will be described. A resin composition of the present embodiment contains the modifying agent of the first embodiment in a proportion of 0.1% to 30% by mass. The resin composition of the present embodiment preferably contains, with respect to 100 parts by mass (100% by mass) in total of the polyolefin resin and the modifying agent of the first embodiment, the polyolefin resin in a proportion of 99.9 to 70.0 parts by mass (% by mass) and the modifying agent of the first embodiment in a proportion of 0.1 to 30.0 parts by mass (% by mass). By specifying in these ranges, the production stability of the resin composition can be further improved.

The resin composition of the present embodiment can also purposively contain other agents. Examples of such other agents include heat stabilizers, antioxidants, neutralizers, lubricants, weatherproofing agents, ultraviolet absorbents, and antiblocking agents. It is preferable that the content of these other agents is made as low as possible. Particularly, an antiblocking agent to be contained is preferably, oxide-based inorganic particles of, for example, silica, diatomaceous earth, alumina, iron oxide, or ferrite, silicate-based inorganic particles of, for example, zeolite, talc, wollastonite, mica, or clay, or organic crosslinked particles, such as crosslinked silicone particles, crosslinked polytriazine particles, crosslinked polyacryl particles, or crosslinked polystyrene particles. These specific examples may be used singly or concurrently in two or more. In the case of using the antiblocking agent as the other agents, the resin composition preferably contains the antiblocking agent in a proportion of 0.1% to 30.0% by mass. When the total content of the polyolefin resin and the antiblocking agent is taken as 100 parts by mass (100% by mass), the antiblocking agent is contained preferably of 0.1 to 30.0 parts by mass (% by mass) with respect to 99.9 to 70.0 parts by mass (% by mass) of the polyolefin resin. By specifying in such a range, the antiblocking agent can exhibit its action and effect without inhibiting the advantageous effects of the present invention.

The resin composition of the present embodiment itself can be prepared by a well-known method. Examples of the method include (1) a method of previously fabricating a master batch containing a polyolefin resin and the modifying agent of the first embodiment in a high concentration, and mixing the master batch with the polyolefin resin to thereby make a resin composition containing the modifying agent in a predetermined concentration, and (2) a method of charging and mixing a polyolefin resin and the modifying agent of the first embodiment in a mixing machine, such as a tumbler blender, a Supermixer, or a Henschel mixer, and granulating the mixture while melt kneading the mixture by an extruding machine, such as a single-screw extruder or a multi-screw extruder, to thereby make a resin composition containing the modifying agent in a predetermined concentration. The method also includes (3) a method of mixing the modifying agent of the first embodiment through a side feed or liquid injection in a polyolefin resin made into a melt state by an extruding machine, such as a single-screw extruder or a multi-screw extruder, and granulating the mixture while melt kneading the mixture to thereby make a resin composition containing the modifying agent in a predetermined concentration. The method further includes (4) a method of combining the above methods of (2) and (3). The production of the master batch in the above method of (1) can be carried out as in the above methods of (2), (3) and (4). As means of mixing the polyolefin resin with the modifying agent of the first embodiment, which method is to be adopted from among the mixing by a mixing machine, such as a tumbler blender, a Supermixer, or a Henschel mixer, and the side feed and the liquid injection, can be determined according to the conditions of the polyolefin resin and the modifying agent of the first embodiment. In the case of being solid, there can be adopted the mixing by a mixing machine such as a tumbler blender, a Supermixer, or a Henschel mixer, or the side feed. In the case of being liquid, there can be adopted the liquid injection or the mixing machine such as a Supermixer or a Henschel mixer. For the case of being a solid material, the solid material can also be mixed as a liquid or a liquid material after the solid material is dissolved or dispersed in a liquid material.

The resin composition of the present embodiment is finally formed into a film shape and applied as a modified polyolefin resin film.

Third Embodiment

Next, a third embodiment that embodies a modified polyolefin resin film according to the present invention (hereinafter referred to simply as film) will be described. The film of the present embodiment is formed into a film shape by using the resin composition of the second embodiment. The film of the present embodiment contains the modifying agent of the first embodiment in a proportion of 0.1% to 5.0% by mass. When the total content of the polyolefin resin and the modifying agent of the first embodiment is taken as 100 parts by mass (100% by mass), the film of the present embodiment preferably contains the polyolefin resin in a proportion of 99.9 to 95.0 parts by mass (% by mass) and the modifying agent of the first embodiment in a proportion of 0.1 to 5.0 parts by mass (% by mass). By specifying in such a range, the film forming stability of the film can be further improved.

As a method of forming the film of the present embodiment, a well-known method can be used, and examples of such a forming method include inflation, such as air-cooling inflation, air-cooling two-stage inflation, air-cooling three-stage inflation, or water-cooling inflation, and T-die forming using, as a T die, a straight manifold type, a coat hanger type, or a combination thereof. For forming the film of the present embodiment, either a non-stretching method or a stretching method may be used, and examples of such a stretching method includes a successive biaxial stretching method, a simultaneous biaxial stretching method, and a tubular biaxial stretching method.

As described in the first embodiment, the film of the present embodiment has a content of 0.02% by mass or lower, preferably 0.01% by mass or lower of the diethanolamine compound or the diethanolamide compound, and is more preferably substantially free of the diethanolamine compound or the diethanolamide compound. With 0.01% by mass or lower of the diethanolamine compound or the diethanolamide compound in the film, the transparency of the film can be improved.

Further, the film of the present embodiment has a content of 0.004% by mass or lower, preferably 0.001% by mass or lower of the alkylsulfonic acid alkali metal salt, and is more preferably substantially free of the alkylsulfonic acid alkali metal salt. With 0.004% by mass or lower of the alkylsulfonic acid alkali metal salt in the film, the film forming stability of the film can be improved.

The lower the haze value of the film of the present embodiment, the better in order to improve the transparency. More specifically, the haze value is preferably lower than 10% and more preferably lower than 5%. The haze value is a haze value (%) prescribed in JIS K7136 (2000). Here, the JIS K7136 (2000) corresponds to ISO 14782, published in 1999 as first version, Plastics-Determination of haze for transparent materials, and technical contents of the both are equal.

The lower limit of the film thickness of the film of the present embodiment is not especially limited, but is preferably 5 μm or larger, more preferably 10 μm or larger, and still more preferably 15 μm or larger. In the case of being 5 μm or larger, the film forming stability can be further improved. The upper limit of the film thickness is not especially limited, but is preferably 250 μm or smaller, more preferably 200 μm or smaller, and still more preferably 150 μm or smaller. In the case of being 250 μm or smaller, the transparency can be further improved.

Fourth Embodiment

Finally, a fourth embodiment that embodies a laminated film according to the present embodiment will be described. The laminated film according to the present invention is a laminated film having two or more layers, and at least either one surface layer of the laminated film is formed by using the resin composition of the second embodiment. Examples of a material constituting the other layer not using the resin composition of the second embodiment includes thermoplastic resins, adhesives, anchor coating agents, adhesive resins, and metals, such as aluminum. Specific examples of such thermoplastic resins include the above-mentioned polyolefin resin; polyesters, such as polyethylene terephthalate; polyamides, such as nylon 6; polyvinyl alcohol; polystyrene; and acrylic resins, such as polymethyl methacrylate. Such thermoplastic resins may also purposively contain additives. Examples of such additives include heat stabilizers, antioxidants, neutralizers, lubricants, weatherproofing agents, ultraviolet absorbents, antiblocking agents, antistatic agents, and antifogging agents.

The laminated film of the present embodiment itself can be produced by a well-known method. Examples of such a production method include a dry lamination method, a sandwich lamination method, an extrusion lamination method, and a coextrusion method. In the case where a laminated film is produced by the dry lamination method, the sandwich lamination method, or the extrusion lamination method, a well-known polyurethane-based adhesive, organotitanium-based anchor coating agent, isocyanate-based anchor coating agent, adhesive resin or the like can be used. In the production by the coextrusion method, inflation and T-die forming described above can be used, and either forming method of non-stretching and stretching using the stretching method described above can also be used.

The laminated film of the present embodiment contains the modifying agent of the first embodiment in a proportion of 0.01% to 5.0% by mass in the whole laminated film. When the total content of the polyolefin resin and the modifying agent of the first embodiment in the laminated film is taken as 100 parts by mass (% by mass), the laminated film of the present embodiment preferably contains the polyolefin resin in a proportion of 99.99 to 95.0 parts by mass (% by mass) and the modifying agent of the first embodiment in a proportion of 0.01 to 5.0 parts by mass (% by mass). By specifying in these ranges, the film forming stability of the laminated film can be further improved.

In the laminated film of the present embodiment, at least either one surface layer thereof contains the modifying agent of the first embodiment, and a layer adjacent to the one surface layer may also contain the modifying agent.

The modifying agent, the resin composition, the film, and the laminated film of the present embodiments can provide the following effects.

(1) In the above embodiments, the modifying agent is a partial ester of a tri- to hexahydric polyol with a straight chain aliphatic carboxylic acid having 8 to 22 carbon atoms, wherein the partial ester contains 70% by mass or more in total of monoester and diester, and the mass ratio of the content of the monoester to the content of the diester is monoester/diester=30/70 to 86/14. The modifying agent is applied to a polyolefin resin film in which the content of a predetermined diethanolamine compound or diethanolamide compound is 0.02% by mass or lower, and the content of an alkylsulfonic acid alkali metal salt is 0.004% by mass or lower.

Therefore, the polyolefin resin film can be imparted with excellent antifogging property without adverse effects on the transparency and the film forming stability.

Further, the polyolefin resin film containing the modifying agent can be imparted with excellent antistaticity.

Further, no adverse effects are imparted on production of the resin composition such as the master batch.

EXAMPLES

Examples will now be given below to describe the features and effects of the present invention more specifically, but the present invention is not limited to these examples. In the following description of working examples and comparative examples, parts means parts by mass and % means % by mass.

Experimental Part 1 (Preparation of Modifying Agent for Polyolefin Resin Film)

Example 1

36.96 parts of diglycerol monolaurate, 47.04 parts of diglycerol dilaurate, 3 parts of diglycerol, and 13 parts of diglycerol trilaurate were homogeneously mixed to thereby prepare a modifying agent for a polyolefin resin film (A-1) of Example 1.

The modifying agent for a polyolefin resin film (A-1) had a permeation amount of 42 mg/g and an HLB of 7.3.

Examples 2 to 8 and Comparative Examples 1 to 6

Modifying agents for a polyolefin resin film (A-2) to (A-8) and (a-1) to (a-6) of Examples 2 to 8 and Comparative Examples 1 to 6 were prepared as in the modifying agent for a polyolefin resin film (A-1) of Example 1. The respective contents of the prepared modifying agents for a polyolefin resin film are shown in Table 1 with that of the modifying agent for a polyolefin resin film (A-1) of Example 1. In Table 1, there are shown the kinds of tri- to hexahydric polyols and aliphatic carboxylic acids constituting partial esters, the ratios and contents of monoester (mono(m)) and diester (di(d)) in the partial esters, and the permeation amounts and the HLB values of the partial esters.

Experimental Part 2 (Production of Composition for Polyolefin Resin Film (Masterbatch))

Example 9

A composition for a resin film was produced as a masterbatch (M-1) by using 88.5 parts of an ethylene-(1-hexene) copolymer (density: 0.930 g/cm$^3$, MFR: 1.0 g/10 min, ethylene copolymerization ratio: 96%) (R-1) as a polyolefin resin, 10 parts of the modifying agent for a polyolefin resin film (A-1) prepared in Experimental Part 1, and 1.5 parts of an antiblocking agent (B-1).

Examples 10 to 16 and Comparative Examples 7 to 15

Masterbatches (M-2) to (M-8) and (m-1) to (m-9) of Examples 10 to 16 and Comparative Examples 7 to 15 were produced as in the masterbatch (M-1) of Example 9. The respective contents of the produced masterbatches are shown in Table 2 with that of the masterbatch (M-1) of Example 9. In Table 2, there are shown the kinds and contents of the modifying agents, the kinds and contents of the polyolefin resins, and the kinds and contents of other agents in the composition for a polyolefin resin film (masterbatches).

TABLE 1

| Category | Modifying agent | Partial ester of tri- to hexahydric polyol with aliphatic carboxylic acid | | Partial ester ratio | | | Permeation | |
|---|---|---|---|---|---|---|---|---|
| | | Tri- to hexahydric polyol | Aliphatic carboxylic acid | Mono(m) (mass ratio) | Di(d) (mass ratio) | Mono(m) + di(d) (% by mass) | amount (mg/g) | HLB |
| Ex. 1 | A-1 | Diglycerol | Lauric acid | 44 | 56 | 84 | 42 | 7.3 |
| Ex. 2 | A-2 | Diglycerol | Stearic acid/palmitic acid = 7/3*[1] | 45 | 55 | 79 | 73 | 5.7 |
| Ex. 3 | A-3 | Diglycerol | Oleic acid | 43 | 57 | 72 | 60 | 5.7 |
| Ex. 4 | A-4 | Diglycerol | Caprylic acid | 83 | 17 | 95 | 33 | 8.4 |
| Ex. 5 | A-5 | Diglycerol | Docosanoic acid | 70 | 30 | 95 | 87 | 5.1 |
| Ex. 6 | A-6 | Sorbitan | Lauric acid | 50 | 50 | 80 | 71 | 6.6 |
| Ex. 7 | A-7 | Tetraglycerol | Stearic acid/palmitic acid = 7/3*[1] | 32 | 68 | 90 | 65 | 7.4 |
| Ex. 8 | A-8 | Glycerol | Oleic acid | 38 | 62 | 70 | 123 | 2.8 |
| Com. Ex. 1 | a-1 | Diglycerol | lauric acid | 88 | 12 | 90 | 14 | 9.4 |
| Com. Ex. 2 | a-2 | Diglycerol | Stearic acid/palmitic acid = 7/3*[1] | 89 | 11 | 92 | 16 | 8.7 |
| Com. Ex. 3 | a-3 | Diglycerol | Hexanoic acid | 95 | 5 | 80 | 12 | 10.7 |
| Com. Ex. 4 | a-4 | Propylene glycol | Oleic acid | 96 | 4 | 95 | 400 | 3.6 |
| Com. Ex. 5 | a-5 | Glycerol | Oleic acid | 0 | 100 | 9 | 230 | 1.9 |
| Com. Ex. 6 | a-6 | Decaglycerol | Isostearic acid | 37 | 27 | 64 | 35 | 13.7 |

In Table 1, the following symbols indicate the following substances.
*[1]mass ratio of aliphatic carboxylic acids
A-1: a partial ester of diglycerol with lauric acid
A-2: a partial ester of diglycerol with stearic acid/palmitic acid (7/3 (indicated in mass ratio; the same applies hereinafter))
A-3: a partial ester of diglycerol with oleic acid
A-4: a partial ester of diglycerol with caprylic acid
A-5: a partial ester of diglycerol with docosanoic acid
A-6: a partial ester of sorbitan with lauric acid
A-7: a partial ester of tetraglycerol with stearic acid/palmitic acid (7/3)
A-8: a partial ester of glycerol with oleic acid
a-1: a partial ester of diglycerol with lauric acid
a-2: a partial ester of diglycerol with stearic acid/palmitic acid (7/3)
a-3: a partial ester of diglycerol with hexanoic acid
a-4: a partial ester of propylene glycol with oleic acid
a-5: a partial ester of glycerol with oleic acid
a-6: a partial ester of decaglycerol with isostearic acid

TABLE 2

Makeup of composition for polyolefin resin film

| Category | Masterbatch | Modifying agent | Concentration of modifying agent (% by mass) | Other modifying agent | Concentration of other modifying agent (% by mass) | Polyolefin resin | Concentration of polyolefin resin (% by mass) | Antiblocking agent | Concentration of antiblocking agent (% by mass) |
|---|---|---|---|---|---|---|---|---|---|
| Ex. 9 | M-1 | A-1 | 10 | | | R-1 | 88.5 | B-1 | 1.5 |
| Ex. 10 | M-2 | A-2 | 28 | | | R-5 | 72 | — | — |
| Ex. 11 | M-3 | A-3 | 15 | | | R-4 | 85 | — | — |
| Ex. 12 | M-4 | A-4 | 4 | | | R-3 | 96 | — | — |
| Ex. 13 | M-5 | A-5 | 10 | | | R-2 | 90 | — | — |
| Ex. 14 | M-6 | A-6 | 10 | | | R-1 | 90 | — | — |
| Ex. 15 | M-7 | A-7 | 10 | | | R-1 | 90 | — | — |
| Ex. 16 | M-8 | A-8 | 10 | | | R-1 | 90 | — | — |
| Com. Ex. 7 | m-1 | a-1 | 10 | | | R-1 | 90 | — | — |
| Com. Ex. 8 | m-2 | a-2 | 10 | | | R-1 | 90 | — | — |
| Com. Ex. 9 | m-3 | a-3 | 10 | | | R-1 | 90 | — | — |
| Com. Ex. 10 | m-4 | a-4 | 10 | | | R-1 | 90 | — | — |
| Com. Ex. 11 | m-5 | a-5 | 10 | | | R-1 | 90 | — | — |
| Com. Ex. 12 | m-6 | a-6 | 10 | | | R-1 | 90 | — | — |
| Com. Ex. 13 | m-7 | A-2 | 5.4 | a-7 | 4.6 | R-1 | 90 | — | — |
| Com. Ex. 14 | m-8 | A-1 | 7.5 | a-8 | 2.5 | R-1 | 90 | — | — |
| Com. Ex. 15 | m-9 | A-2 | 1.25 | a-7 | 1.05 | R-1 | 90 | — | — |
| | | | | a-9 | 7.7 | | | | |

In Table 2, the following symbols indicate the following substances.
R-1: an ethylene-(1-hexene) copolymer (density: 0.930 g/cm$^3$, MFR: 1.0 g/10 min, ethylene copolymerization ratio: 96%)
R-2: an ethylene-(1-butene) copolymer (density: 0.920 g/cm$^3$, MFR: 2.1 g/10 min, ethylene copolymerization ratio: 95%)
R-3: an ethylene polymer (density: 0.93 g/cm$^3$, MFR: 4.0 g/10 min, ethylene copolymerization ratio: 100%)
R-4: an ethylene-propylene copolymer (density: 0.90 g/cm$^3$, MFR: 7.0 g/10 min, ethylene copolymerization ratio: 4%)
R-5: an ethylene-vinyl acetate copolymer (density: 0.936 g/cm$^3$, MFR: 3.0 g/10 min, ethylene copolymerization ratio: 85%)
B-1: silica (average particle diameter: 3 μm, amorphous)
a-7: stearyldiethanolamine
a-8: sodium tetradecylsulfonate
a-9: stearyldiethanolamine monostearate/stearyldiethanolamine distearate (57/33 in mass ratio)

Experimental Part 3 (Evaluation of Masterbatch)

Evaluation of the Masterbatch Producing Stability

When in Experimental Part 2, the masterbatches were produced, the masterbatch producing stability was visually observed and evaluated based on the following criteria. The evaluation results are shown in Table 3.

The evaluation criteria of the masterbatch producing stability
- ○ (good): the masterbatch was stably obtained without occurrence of vent-up and strand unruly motion in the production thereof.
- x (poor): the masterbatch was not stably obtained with occurrence of vent-up and strand unruly motion in the production thereof.

TABLE 3

| Category | Masterbatch | Production stability of masterbatch |
|---|---|---|
| Ex. 9 | M-1 | ○ |
| Ex. 10 | M-2 | ○ |
| Ex. 11 | M-3 | ○ |
| Ex. 12 | M-4 | ○ |
| Ex. 13 | M-5 | ○ |
| Ex. 14 | M-6 | ○ |
| Ex. 15 | M-7 | ○ |
| Ex. 16 | M-8 | ○ |
| Com. Ex. 7 | m-1 | x |
| Com. Ex. 8 | m-2 | x |
| Com. Ex. 9 | m-3 | x |
| Com. Ex. 10 | m-4 | ○ |
| Com. Ex. 11 | m-5 | ○ |
| Com. Ex. 12 | m-6 | ○ |
| Com. Ex. 13 | m-7 | ○ |

TABLE 3-continued

| Category | Masterbatch | Production stability of masterbatch |
|---|---|---|
| Com. Ex. 14 | m-8 | ○ |
| Com. Ex. 15 | m-9 | ○ |

Experimental Part 4 (Production of Modified Polyolefin Resin Film)

Example 17

95 parts of the ethylene-(1-hexene) copolymer (density: 0.930 g/cm$^3$, MFR: 1.0 g/10 min, ethylene copolymerization ratio: 96%) (R-1) as a polyolefin resin and 5 parts of the masterbatch (M-1) prepared in Experimental Part 2 were mixed by a tumbler so that the concentration of the modifying agent for a polyolefin resin film became 0.5 part (% by mass). The mixture was extruded under cooling at 30° C. by a T-die method to thereby produce a polyolefin resin film (N-1) of 80 μm.

Examples 18 to 24 and Comparative Examples 16 to 24

Polyolefin resin films (N-2) to (N-8) and (n-1) to (n-9) of Examples 18 to 24 and Comparative Examples 16 to 24 were produced as in the polyolefin resin film (N-1) of Example 17. The respective contents of the produced polyolefin resin films are shown in Table 4 with that of the polyolefin resin film (N-1) of Example 17. In Table 4, there are shown the kinds and contents of the masterbatches, the concentrations of the modifying agents, the kinds and concentrations of the polyolefin resins in the polyolefin resin films, and the thicknesses of the films.

TABLE 4

| | | | Makeup of polyolefin resin film | | | | |
|---|---|---|---|---|---|---|---|
| Category | Polyolefin resin film | Masterbatch | Concentration of modifying agent (% by mass) | Concentration of other modifying agent (% by mass) | Polyolefin resin | Concentration of polyolefin resin (% by mass) | Film thickness (μm) |
| Ex. 17 | N-1 | M-1 | 0.5 | | R-1 | 99.5 | 80 |
| Ex. 18 | N-2 | M-2 | 2.8 | | R-5 | 97.2 | 30 |
| Ex. 19 | N-3 | M-3 | 4.5 | | R-4 | 95.5 | 10 |
| Ex. 20 | N-4 | M-4 | 0.3 | | R-3 | 99.7 | 40 |
| Ex. 21 | N-5 | M-5 | 2.0 | | R-2 | 98.0 | 40 |
| Ex. 22 | N-6 | M-6 | 0.1 | | R-1 | 99.9 | 40 |
| Ex. 23 | N-7 | M-7 | 5.0 | | R-1 | 95.0 | 40 |
| Ex. 24 | N-8 | M-8 | 5.0 | | R-1 | 95.0 | 40 |
| Com. Ex. 16 | n-1 | m-1 | 2.0 | | R-1 | 98.0 | 40 |
| Com. Ex. 17 | n-2 | m-2 | 2.0 | | R-1 | 98.0 | 40 |
| Com. Ex. 18 | n-3 | m-3 | 2.0 | | R-1 | 98.0 | 40 |
| Com. Ex. 19 | n-4 | m-4 | 4.0 | | R-1 | 96.0 | 40 |
| Com. Ex. 20 | n-5 | m-5 | 4.0 | | R-1 | 96.0 | 40 |
| Com. Ex. 21 | n-6 | m-6 | 1.0 | | R-1 | 99.0 | 40 |
| Com. Ex. 22 | n-7 | m-7 | 1.35 | 1.15 (a-7) | R-1 | 97.5 | 40 |
| Com. Ex. 23 | n-8 | m-8 | 3.0 | 1.0 (a-8) | R-1 | 96.0 | 40 |
| Com. Ex. 24 | n-9 | m-9 | 0.375 | 0.315 (a-7) 2.31 (a-9) | R-1 | 97.0 | 40 |

Experimental Part 5 (Evaluation of Modified Polyolefin Resin Film)

Evaluation of the Antifogging Property

The polyolefin resin films produced in Experimental Part 4 were humidity conditioned under the condition of 20° C. and a relative humidity of 65% for 24 hours, and thereafter adhered on a beaker having water at 20° C. put therein; the beaker was placed in an atmosphere of 5° C. for 24 hours; and the degree of deposition of water droplets on the surface of the beaker on which the film is adhered was observed and the antifogging property was evaluated based on the following criteria. The results are shown in Table 5.

Evaluation Criteria of the Antifogging Property
  ○○ (excellent): exhibiting no deposition of water droplets and being transparent; being remarkably excellent in the antifogging property
  ○ (good): exhibiting deposition of large water droplets, but being transparent; being excellent in the antifogging property
  x (poor): exhibiting a large number of small water droplets and being opaque; being inferior in the antifogging property Evaluation of the Transparency The polyolefin resin films produced in Experimental Part 4 were humidity conditioned under the condition of 20° C. and a relative humidity of 65% for 24 hours, and thereafter, the haze value was measured by using a haze meter (trade name NDH-5000, manufactured by Nippon Denshoku Industries Co., Ltd.) and by the method according to JIS K7136:2000, and the transparency was evaluated based on the following criteria. The evaluation results are shown in Table 5.

Evaluation Criteria of the Transparency
  ○○ (excellent): being lower than 5% (being excellent in the transparency)
  ○ (good): being 5% or higher and lower than 10% (being good in the transparency)
  x (poor): being 10% or higher (being inferior in the transparency)

Evaluation of the Antistaticity

The polyolefin resin films produced in Experimental Part 4 were humidity conditioned under the condition of 20° C. and a relative humidity of 65% for 24 hours, and thereafter, the surface specific resistance ($\Omega/\square$) thereof was measured under the same condition by using a surface resistance meter (trade name: Super Megohmmeter SM-8220, manufactured by Hioki E.E. Corp.), and the antistaticity was evaluated based on the following criteria. The results are shown in Table 5.

Evaluation Criteria of the Antistaticity
  ○○ (excellent): the surface specific resistance was lower than $1\times10^{12}\Omega/\square$
  ○ (good): the surface specific resistance was $1\times10^{12}\Omega/\square$ or higher and lower than $1\times 10^{13}\Omega/\square$
  x (poor): the surface specific resistance was $1\times10^{13}\Omega/\square$ or higher Evaluation of the Film Forming Stability When the polyolefin resin films were formed in Experimental Part 4, the film forming stability of the films was visually observed, and evaluated based on the following criteria. The evaluation results are shown in Table 5.

Evaluation Criteria of the Film Forming Stability
  ○ (good): the formed film exhibited no extrusion fluctuation, and the film having a stable film thickness was obtained.
  x (poor): the formed film exhibited extrusion fluctuation, and no film having a stable film thickness was obtained.

TABLE 5

| Category | Polyolefin resin film | Antifogging property | Transparency | Antistaticity | Film forming stability |
|---|---|---|---|---|---|
| Ex. 17 | N-1 | ⊙⊙ | ⊙⊙ | ⊙⊙ | ○ |
| Ex. 18 | N-2 | ⊙⊙ | ⊙⊙ | ⊙⊙ | ○ |
| Ex. 19 | N-3 | ⊙⊙ | ⊙⊙ | ⊙⊙ | ○ |
| Ex. 20 | N-4 | ⊙⊙ | ⊙⊙ | ⊙⊙ | ○ |
| Ex. 21 | N-5 | ⊙⊙ | ⊙⊙ | ⊙⊙ | ○ |
| Ex. 22 | N-6 | ○ | ⊙⊙ | ○ | ○ |
| Ex. 23 | N-7 | ○ | ⊙⊙ | ○ | ○ |
| Ex. 24 | N-8 | ○ | ○ | ○ | ○ |
| Com. Ex. 16 | n-1 | ⊙⊙ | ⊙⊙ | ⊙⊙ | x |
| Com. Ex. 17 | n-2 | ⊙⊙ | ⊙⊙ | ⊙⊙ | x |
| Com. Ex. 18 | n-3 | ⊙⊙ | ⊙⊙ | ⊙⊙ | x |
| Com. Ex. 19 | n-4 | x | ⊙⊙ | x | ○ |
| Com. Ex. 20 | n-5 | x | ○ | ○ | ○ |
| Com. Ex. 21 | n-6 | x | ⊙⊙ | x | ○ |
| Com. Ex. 22 | n-7 | ○ | x | ⊙⊙ | ○ |
| Com. Ex. 23 | n-8 | ⊙⊙ | ⊙⊙ | ⊙⊙ | x |
| Com. Ex. 24 | n-9 | ○ | x | ⊙⊙ | ○ |

Experimental Part 6 (Production of Laminated Film (No. 1))

Example 25

95 parts of the ethylene-(1-hexene) copolymer (density: 0.930 g/cm$^3$, MFR: 1.0 g/10 min, ethylene copolymerization ratio: 96%) (R-1) as a polyolefin resin and 5 parts of the masterbatch (M-1) produced in Experimental Part 2 were mixed so that the concentration of the modifying agent for a polyolefin resin film (A-1) in the film became 0.5 part (% by mass). The obtained mixture was used as an outer layer (surface layer 1: layer A); and the ethylene-(1-hexene) copolymer (R-1) was used as a middle layer (layer B) and the other outer layer (surface layer 2: layer C). The layers A to C were coextruded by a T-die method under cooling at 30° C. to thereby produce a laminated film (S-1) having a thickness of 100 μm and having three layers. The ratio of thicknesses of the layers was made to be layer A/layer B/layer C=1/8/1.

Examples 26 to 35 and Comparative Examples 25 to 34

Laminated films (S-2) to (S-11) and (s-1) to (s-10) of Examples 26 to 35 and Comparative Examples 25 to 34 were produced as in the production of the laminated film of Example 25. The respective contents of the produced laminated films are shown in Table 6 with that of the laminated film (S-1) of Example 25. In Table 6, there are shown the kinds of the masterbatches, the polyolefin resins, and the modifying agents constituting the each layer, the concentrations of the modifying agents of the each layer, the ratios of thicknesses of the layers, the film thicknesses of the laminated films, and the concentrations of the modifying agents in the laminated films.

TABLE 6

| Category | Laminated film | Outer layer (Layer A) | | | | | | Middle layer (Layer B) | | | |
|---|---|---|---|---|---|---|---|---|---|---|---|
| | | Masterbatch | Polyolefin resin | Modifying agent | Concentration of modifying agent (% by mass) | Other Modifying agent | Concentration of other Modifying agent (% by mass) | Masterbatch | Polyolefin resin | Modifying agent | Concentration of modifying agent (% by mass) |
| Ex. 25 | S-1 | M-1 | R-1 | A-1 | 0.5 | | | — | R-1 | — | — |
| Ex. 26 | S-2 | M-2 | R-5 | A-2 | 2.1 | | | — | R-5 | — | — |
| Ex. 27 | S-3 | M-3 | R-4 | A-3 | 3.0 | | | M-3 | R-4 | A-3 | 0.6 |
| Ex. 28 | S-4 | M-4 | R-3 | A-4 | 2.0 | | | — | R-3 | — | — |
| Ex. 29 | S-5 | M-5 | R-2 | A-5 | 2.0 | | | — | R-2 | — | — |
| Ex. 30 | S-6 | M-3 | R-4 | A-3 | 3.0 | | | — | R-6 | — | — |
| Ex. 31 | S-7 | M-1 | R-1 | A-1 | 2.0 | | | — | R-7 | — | — |
| Ex. 32 | S-8 | M-1 | R-5 | A-1 | 5.0 | | | M-1 | R-1 | A-1 | 4 |
| Ex. 33 | S-9 | M-6 | R-1 | A-6 | 0.1 | | | — | R-1 | — | — |
| Ex. 34 | S-10 | M-7 | R-1 | A-7 | 5.0 | | | — | R-1 | — | — |
| Ex. 35 | S-11 | M-8 | R-1 | A-8 | 5.0 | | | — | R-1 | — | — |
| Com. Ex. 25 | s-1 | m-1 | R-1 | a-1 | 2.0 | | | — | R-1 | — | — |
| Com. Ex. 26 | s-2 | m-2 | R-1 | a-2 | 2.0 | | | — | R-1 | — | — |
| Com. Ex. 27 | s-3 | m-3 | R-1 | a-3 | 2.0 | | | — | R-1 | — | — |
| Com. Ex. 28 | s-4 | m-4 | R-1 | a-4 | 4.0 | | | — | R-1 | — | — |
| Com. Ex. 29 | s-5 | m-5 | R-1 | a-5 | 4.0 | | | — | R-1 | — | — |
| Com. Ex. 30 | s-6 | m-6 | R-1 | a-6 | 5 | | | — | R-1 | — | — |
| Com. Ex. 31 | s-7 | m-7 | R-1 | A-2 | 2.7 | a-7 | 2.3 | M-1 | R-1 | A-1 | 4 |
| Com. Ex. 32 | s-8 | m-8 | R-1 | A-1 | 3.75 | a-8 | 1.25 | — | R-1 | — | — |
| Com. Ex. 33 | s-9 | m-9 | R-1 | A-2 | 1 | a-7 | 0.84 | M-1 | R-1 | A-1 | 4 |
| | | | | | | a-9 | 6.16 | | | | |
| Com. Ex. 34 | s-10 | m-8 | R-1 | A-1 | 0.75 | a-8 | 0.25 | — | R-1 | — | — |

TABLE 6-continued

| | | Outer layer (Layer C) | | | Ratio of thicknesses in laminated film | | | Laminated film thickness (μm) | Concentration of modifier in laminated film (% by mass) |
|---|---|---|---|---|---|---|---|---|---|
| Category | Masterbatch | Polyolefin resin | Modifying agent | Concentration of modifying agent (% by mass) | Layer A | Layer B | Layer C | | |
| Ex. 25 | — | R-1 | — | — | 1.0 | 8.0 | 1.0 | 100 | 0.05 |
| Ex. 26 | M-2 | R-5 | A2 | 2.1 | 3.0 | 4.0 | 3.0 | 20 | 1.26 |
| Ex. 27 | — | R-4 | — | — | 0.5 | 9.0 | 0.5 | 240 | 0.69 |
| Ex. 28 | — | R-3 | — | — | 1.5 | 7.0 | 1.5 | 100 | 0.30 |
| Ex. 29 | — | R-2 | — | — | 1.5 | 7.0 | 1.5 | 100 | 0.30 |
| Ex. 30 | — | R-4 | — | — | 2.0 | 6.0 | 2.0 | 100 | 0.60 |
| Ex. 31 | — | R-8 | — | — | 2.0 | 6.0 | 2.0 | 100 | 0.40 |
| Ex. 32 | M-1 | R-5 | A1 | 5 | 1.0 | 8.0 | 1.0 | 40 | 4.20 |
| Ex. 33 | — | R-1 | — | — | 4.0 | 2.0 | 4.0 | 100 | 0.04 |
| Ex. 34 | — | R-1 | — | — | 2.0 | 6.0 | 2.0 | 100 | 1.00 |
| Ex. 35 | — | R-1 | — | — | 2.0 | 6.0 | 2.0 | 100 | 1.00 |
| Com. Ex. 25 | — | R-1 | — | — | 2.0 | 6.0 | 2.0 | 100 | 0.40 |
| Com. Ex. 26 | — | R-1 | — | — | 2.0 | 6.0 | 2.0 | 100 | 0.40 |
| Com. Ex. 27 | — | R-1 | — | — | 2.0 | 6.0 | 2.0 | 100 | 0.40 |
| Com. Ex. 28 | — | R-1 | — | — | 2.0 | 6.0 | 2.0 | 100 | 0.80 |
| Com. Ex. 29 | — | R-1 | — | — | 2.0 | 6.0 | 2.0 | 100 | 0.80 |
| Com. Ex. 30 | — | R-1 | — | — | 1.0 | 8.0 | 1.0 | 100 | 0.50 |
| Com. Ex. 31 | — | R-1 | — | — | 1.0 | 8.0 | 1.0 | 100 | 3.70 |
| Com. Ex. 32 | — | R-1 | — | — | 1.0 | 8.0 | 1.0 | 100 | 0.50 |
| Com. Ex. 33 | — | R-1 | — | — | 1.0 | 8.0 | 1.0 | 100 | 4.00 |
| Com. Ex. 34 | — | R-1 | — | — | 1.0 | 8.0 | 1.0 | 100 | 0.10 |

Experimental Part 7 (Evaluation of Laminated Film (No. 1))

For the laminated films produced in Experimental Part 6, there were evaluated, as in Experimental Part 5, the antifogging property, the transparency, the antistaticity, and the film forming stability. The evaluation results are shown in Table 7.

TABLE 7

| Category | Laminated film | Antifogging property | Transparency | Antistaticity | Film forming stability |
|---|---|---|---|---|---|
| Ex. 25 | S-1 | ∞ | ∞ | ∞ | ○ |
| Ex. 26 | S-2 | ∞ | ∞ | ∞ | ○ |
| Ex. 27 | S-3 | ∞ | ∞ | ∞ | ○ |
| Ex. 28 | S-4 | ∞ | ∞ | ∞ | ○ |
| Ex. 29 | S-5 | ∞ | ∞ | ∞ | ○ |
| Ex. 30 | S-6 | ∞ | ∞ | ∞ | ○ |
| Ex. 31 | S-7 | ∞ | ∞ | ∞ | ○ |
| Ex. 32 | S-8 | ∞ | ∞ | ∞ | ○ |
| Ex. 33 | S-9 | ○ | ∞ | ○ | ○ |
| Ex. 34 | S-10 | ○ | ∞ | ○ | ○ |
| Ex. 35 | S-11 | ○ | ○ | ○ | ○ |
| Com. Ex. 25 | s-1 | ∞ | ∞ | ∞ | x |
| Com. Ex. 26 | s-2 | ∞ | ∞ | ∞ | x |
| Com. Ex. 27 | s-3 | ∞ | ∞ | ∞ | x |
| Com. Ex. 28 | s-4 | x | ∞ | x | ○ |
| Com. Ex. 29 | s-5 | x | ○ | ○ | ○ |
| Com. Ex. 30 | s-6 | x | ∞ | x | ○ |
| Com. Ex. 31 | s-7 | ○ | x | ∞ | ○ |
| Com. Ex. 32 | s-8 | ∞ | ∞ | ∞ | x |
| Com. Ex. 33 | s-9 | ○ | x | ∞ | ○ |
| Com. Ex. 34 | s-10 | ∞ | ∞ | ∞ | x |

Experimental Part 8 (Production of Laminated Film (No. 2))

Example 36

On a base film (biaxially stretched polyamide film, thickness: 15 μm) (K-1), there was applied a polyurethane-based adhesive (an aromatic ether-based adhesive (T-1) manufactured by Mitsui Chemicals, Inc., a mixture, whose solid content concentration was adjusted to 20% with ethyl acetate, of trade name Takelac A-969V/Takenate A-5 (3/1 in mass ratio) so that the coating amount became 4 g/m² (solid content). The resultant was dried at 80° C. for 90 sec; thereafter, the resultant was laminated with the polyolefin resin film (N-1) produced in Experimental Part 4 by a nip roll, and left at 40° C. for 24 hours to cure the adhesive to thereby obtain a laminated film (S-12).

Examples 37 to 48 and Comparative Examples 35 to 37

Laminated films (S-13) to (S-24) and (s-11) to (s-13) of Examples 37 to 48 and Comparative Examples 35 to 37 were produced as in the production of the laminated film of Example 36. The respective contents of the produced laminated films are shown in Table 8 with that of the laminated film of Example 36. In Table 8, there are shown the kinds of the polyolefin resin films, the base films, and the adhesives constituting the laminated films.

TABLE 8

| Category | Laminated film | Polyolefin resin film | Base film | Adhesive |
|---|---|---|---|---|
| Ex. 36 | S-12 | N-1 | K-1 | T-1 |
| Ex. 37 | S-13 | N-1 | K-1 | T-2 |
| Ex. 38 | S-14 | N-1 | K-1 | T-3 |
| Ex. 39 | S-15 | N-1 | K-1 | T-4 |
| Ex. 40 | S-16 | N-1 | K-1 | T-5 |
| Ex. 41 | S-17 | N-1 | K-1 | T-6 |
| Ex. 42 | S-18 | N-2 | K-2 | T-1 |
| Ex. 43 | S-19 | N-3 | K-3 | T-1 |
| Ex. 44 | S-20 | N-4 | K-1 | T-1 |
| Ex. 45 | S-21 | N-5 | K-1 | T-1 |
| Ex. 46 | S-22 | N-6 | K-1 | T-1 |
| Ex. 47 | S-23 | N-7 | K-1 | T-1 |
| Ex. 48 | S-24 | N-8 | K-1 | T-1 |
| Com. Ex. 35 | s-11 | n-4 | K-1 | T-1 |
| Com. Ex. 36 | s-12 | n-5 | K-1 | T-1 |
| Com. Ex. 37 | s-13 | n-6 | K-1 | T-1 |

In Table 8, the following symbols indicate the following substances.

K-1: trade name Emblem ON, manufactured by Unitika Ltd., thickness: 15 μm

K-2: trade name E5100, manufactured by Toyobo Co., Ltd., thickness: 12 μm

K-3: trade name Pylen Film-OT P2108, manufactured by Toyobo Co., Ltd., thickness: 30 μm T-1: a polyurethane-based adhesive (an aromatic ether-based adhesive manufactured by Mitsui Chemicals, Inc., a mixture, whose solid content concentration was adjusted to 20% with ethyl acetate, of trade name Takelac A-969V/Takenate A-5 (3/1 in mass ratio))

T-2: a polyurethane-based adhesive (an aromatic ester-based adhesive manufactured by Mitsui Chemicals, Inc., a mixture, whose solid content concentration was adjusted to 20% with ethyl acetate, of trade name Takelac A-515/Takenate A-3 (3/1 in mass ratio))

T-3: a polyurethane-based adhesive (an aliphatic ester-based adhesive manufactured by Mitsui Chemicals, Inc., a mixture, whose solid content concentration was adjusted to 20% with ethyl acetate, of trade name Takelac A-385/Takenate A-50 (3/1 in mass ratio))

T-4: a polyurethane-based adhesive (an aromatic ether-based adhesive manufactured by Mitsui Chemicals, Inc., a mixture, whose solid content concentration was adjusted to 20% with ion-exchange water, of trade name Takelac A-242B/Takenate A-242A (3/1 in mass ratio))

T-5: a polyurethane-based adhesive (an aliphatic ester-based adhesive manufactured by Mitsui Chemicals, Inc., a mixture, whose solid content concentration was adjusted to 20% with ion-exchange water, of trade name Takelac A-695/Takenate A-95 (3/1 in mass ratio))

T-6: a polyurethane-based adhesive (an aromatic ether-based adhesive manufactured by Mitsui Chemicals, Inc., trade name Takelac A-260, whose solid content concentration was adjusted to 20% with ion-exchange water)

Experimental Part 9 (Evaluation of Laminated Film (No. 2))

For the laminated films produced in Experimental Part 8, the antifogging property and the antistaticity were evaluated as in Experimental Part 5. Then, for the transparency, the laminated films were humidity conditioned under the condition of 20° C. and a relative humidity of 65% for 24 hours, and thereafter, the haze value was measured by using a haze meter (trade name NDH-5000, manufactured by Nippon Denshoku Industries Co., Ltd.) and by the method according to JIS K7136:2000, and the transparency was evaluated based on the following criteria. The evaluation results are shown in Table 9.

Evaluation Criteria of the Transparency

○○ (excellent): being lower than 10% (being excellent in the transparency)

○ (good): being 10% or higher and lower than 15% (being good in the transparency)

x (poor): being 15% or higher (being inferior in the transparency)

TABLE 9

| Category | Laminated film | Antifogging property | Transparency | Antistaticity |
|---|---|---|---|---|
| Ex. 36 | S-12 | ○○ | ○○ | ○○ |
| Ex. 37 | S-13 | ○○ | ○○ | ○○ |
| Ex. 38 | S-14 | ○○ | ○○ | ○○ |
| Ex. 39 | S-15 | ○○ | ○○ | ○○ |
| Ex. 40 | S-16 | ○○ | ○○ | ○○ |
| Ex. 41 | S-17 | ○○ | ○○ | ○○ |
| Ex. 42 | S-18 | ○○ | ○○ | ○○ |
| Ex. 43 | S-19 | ○○ | ○○ | ○○ |
| Ex. 44 | S-20 | ○○ | ○○ | ○○ |
| Ex. 45 | S-21 | ○○ | ○○ | ○○ |
| Ex. 46 | S-22 | ○ | ○○ | ○ |
| Ex. 47 | S-23 | ○ | ○○ | ○ |
| Ex. 48 | S-24 | ○ | ○ | ○ |
| Com. Ex. 35 | s-11 | x | ○○ | x |
| Com. Ex. 36 | s-12 | x | ○ | ○ |
| Com. Ex. 37 | s-13 | x | ○○ | x |

As is clear from the evaluation results of Examples to Comparative Examples in Tables 3, 5, 7, and 9 corresponding to Tables 2, 4, 6, and 8, the modifying agent of the present invention can impart an excellent antistaticity and antifogging property to the polyolefin resins without adversely affecting the transparency and the film forming stability intrinsic to the polyolefin resins.

The invention claimed is:

1. A method of modifying a polyolefin resin film using a modifying agent that is a partial ester of diglycerol with a straight chain aliphatic carboxylic acid having 8 to 22 carbon atoms, wherein the partial ester contains 70% by mass or more in total of monoester and diester, the mass ratio of the content of the monoester to the content of the diester is monoester/diester=30/70 to 86/14, wherein the content of a diethanolamine compound having an alkyl group or alkenyl group having 8 to 22 carbon atoms or a diethanolamide compound having an alkyl group or alkenyl group having 8 to 22 carbon atoms in the polyolefin resin film is 0.02% by mass or lower, and the content of an alkylsulfonic acid alkali metal salt in the polyolefin resin film is 0.004% by mass or lower.

2. The method according to claim 1, wherein the mass ratio of the content of the monoester to the content of the diester is monoester/diester=40/60 to 86/14.

3. The method according to claim 1, wherein the partial ester has a permeation amount of 20 mg/g or larger.

4. The method according to claim 1, wherein the partial ester has an HLB of 2 to 8.5.

5. The method according to claim 1, wherein the modifying agent for a polyolefin resin film is applied to a polyolefin resin film substantially free of the diethanolamine compound or the diethanolamide compound and the alkylsulfonic acid alkali metal salt.

6. The method according to claim 1, wherein the polyolefin resin film is a film for food.

7. A resin composition for a polyolefin resin film, comprising 0.1% to 30% by mass of a modifying agent for a polyolefin resin film and 99.9% to 70% by mass of a polyolefin resin, wherein the modifying agent is a partial ester of diglycerol with a straight chain aliphatic carboxylic acid having 8 to 22 carbon atoms, the partial ester contains 70% by mass or more in total of monoester and diester, and the mass ratio of the content of the monoester to the content of the diester is monoester/diester=30/70 to 86/14.

8. A modified polyolefin resin film, comprising 0.1% to 5% by mass of a modifying agent for a polyolefin resin film, wherein
the modifying agent is a partial ester of diglycerol with a straight chain aliphatic carboxylic acid having 8 to 22 carbon atoms, the partial ester contains 70% by mass or more in total of monoester and diester, and the mass ratio of the content of the monoester to the content of the diester is monoester/diester=30/70 to 86/14, and
in the film, the content of a diethanolamine compound having an alkyl group or alkenyl group having 8 to 22 carbon atoms or a diethanolamide compound having an alkyl group or alkenyl group having 8 to 22 carbon atoms is 0.02% by mass or lower, and the content of an alkylsulfonic acid alkali metal salt is 0.004% by mass or lower.

9. The modified polyolefin resin film according to claim 8, wherein the modified polyolefin resin film has a haze value of lower than 10%.

10. A laminated film, comprising a modified polyolefin resin film layer that contains a modifying agent for a polyolefin resin film as at least either one surface layer thereof, wherein
the modifying agent is a partial ester of diglycerol with a straight chain aliphatic carboxylic acid having 8 to 22 carbon atoms, the partial ester contains 70% by mass or more in total of monoester and diester, and the mass ratio of the content of the monoester to the content of the diester is monoester/diester=30/70 to 86/14, and
the laminated film contains 0.01% to 5% by mass of the modifying agent for a polyolefin resin film.

11. A method of modifying a polyolefin resin film using a modifying agent that is a partial ester of diglycerol with a straight chain aliphatic carboxylic acid having 8 to 22 carbon atoms, wherein the partial ester contains 70% by mass or more in total of monoester and diester, the mass ratio of the content of the monoester to the content of the diester is monoester/diester=40/60 to 86/14,
wherein the polyolefin resin film is substantially free of a diethanolamine compound having an alkyl group or alkenyl group having 8 to 22 carbon atoms or a diethanolamide compound having an alkyl group or alkenyl group having 8 to 22 carbon atoms and an alkylsulfonic acid alkali metal salt, the polyolefin resin film being a film for food, and
wherein the partial ester has a permeation amount of 20 mg/g or larger and an HLB of 2 to 8.5.

* * * * *